United States Patent [19]

Pelerin

[11] Patent Number: 5,011,407
[45] Date of Patent: Apr. 30, 1991

[54] CUSTOM DENTAL IMPRESSION TRAY

[76] Inventor: Joseph Pelerin, 3051 E. Pontiac Rd., Auburn Hills, Mich. 48057

[21] Appl. No.: 354,712

[22] Filed: May 22, 1989

[51] Int. Cl.$^5$ .............................................. A61C 9/00
[52] U.S. Cl. .......................................... 433/48; 433/37
[58] Field of Search ...................... 433/71, 48, 41, 37; 128/863

[56] References Cited

U.S. PATENT DOCUMENTS

| | | | |
|---|---|---|---|
| 1,763,553 | 6/1930 | Dennis | 433/37 |
| 2,404,683 | 7/1946 | Barishman | 433/70 |
| 4,227,877 | 10/1980 | Tureaud et al. | 433/37 |
| 4,413,979 | 11/1983 | Ginsburg | 433/48 |
| 4,569,342 | 2/1986 | von Nostitz | 433/48 |
| 4,619,610 | 10/1986 | Pelerin | 433/41 |
| 4,657,509 | 4/1987 | Morris | 433/41 |
| 4,768,951 | 9/1988 | Abiru et al. | 433/48 |

Primary Examiner—Cary E. Stone
Attorney, Agent, or Firm—Gifford, Groh, Sprinkle, Patmore and Anderson

[57] ABSTRACT

The present invention provides a custom impression dental tray having a sheet of thermosetting material. The thermosetting material is preferably polycapractone which becomes pliable at a temperature between 130°–140° F. but becomes rigid at the temperature of the human mouth. An optional separation layer is disposed over one side of the sheet of thermosetting material with a wax or clay-like consistency. In practice, the tray is heated to a temperature of between 115°–150° F. and then molded around the teeth in the patient's mouth (or the impression of the patient's mouth for denture work). After the tray has ridigified, the separation layer and wax covering are removed from the tray thus providing a space for dental impression material to allow a final impression to be made.

1 Claim, 1 Drawing Sheet

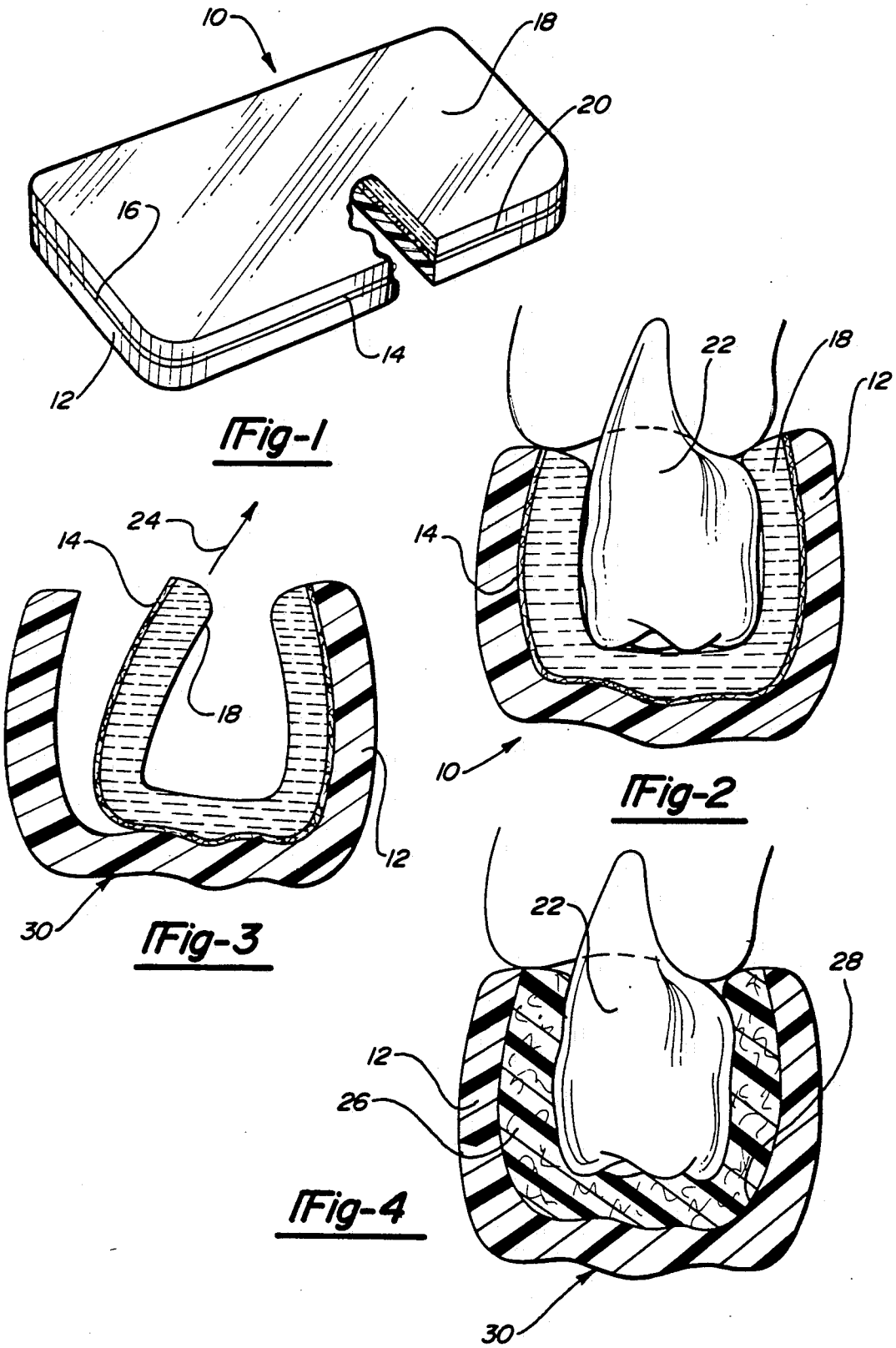

CUSTOM DENTAL IMPRESSION TRAY

BACKGROUND OF THE INVENTION

I. Field of the Invention

The present invention relates to a custom dental impression tray for both crown and bridge prosthesis as well as dentures.

II. Description of the Prior Art

Dental impression trays are necessary to construct both crown and bridge prosthesis as well as dentures. Furthermore, since the human mouth varies from one patient to the next, it is necessary for the dentist to make a custom impression tray before the bridge, crown or dentures can be constructed.

In the previously known methods for constructing custom impression trays, a preliminary model of the mouth is first made by the dentist. Typically, the dentist selects a standard tray which fits within the area of the mouth being treated. This tray is then filled with alginate, pressed into the patient's mouth and allowed to set. Thereafter, the tray is removed and filled with plaster in order to form the preliminary model of the patient's teeth and/or mouth.

After the preliminary plaster model has hardened, thin separating sheets, typically constructed of asbestos, are molded onto the preliminary model in order to form a small space between the teeth or gum area on the model and the outside of the separating sheets.

Thereafter, powdered acrylic and liquid monomer are mixed together until the mixture reaches a putty consistency. The mixture is then molded into a patty which is then molded around the separating sheets of the preliminary model. Upon hardening, the molded acrylic and monomer forms the custom tray.

After the custom tray has hardened, dental impression material is placed in the tray and then positioned within the patient's mouth. The dental impression material fills the space represented by the separating sheets on the preliminary model and, upon hardening, forms a final impression of the desired area of the patient's mouth. The crown, bridge work and/or dentures are formed from this final impression of the patient's mouth.

A primary disadvantage of this previously known method for forming custom dental impression trays is that the procedure is time consuming and tedious. Furthermore, in view of the materials employed and the multiple steps necessary to obtain the custom dental impression tray, this previously known procedure is expensive in material costs.

SUMMARY OF THE PRESENT INVENTION

The present invention provides a custom dental impression tray for crown and bridge prosthesis and/or dentures which overcomes all of the above mentioned disadvantages of the previously known custom dental impression trays.

The dental impression tray of the present invention comprises a sheet of thermosetting material. The thermosetting material is pliable at a temperature in the range of 115°-150° F. but becomes rigid when cooled to the temperature of a human mouth. Preferably, this material is polycapractone although other materials may alternatively be used.

A flexible separation layer overlies and covers one side of the thermosetting sheet. This separation layer is preferably constructed of gauze although other materials may alternatively be used.

A wax or clay-like covering then covers the other side of the separation layer. This covering is pliable at the same temperature that the thermosetting material becomes pliable so that the layer and thermosetting sheet can be simultaneously shaped and molded. Additionally, this covering has a substantially uniform thickness.

In practice, the tray is heated to a temperature of 130°-140° F. until both the thermosetting sheet as well as the wax covering become pliable. For crown and bridge work, the pliable tray is then molded around the affected area of the patient's mouth and allowed to cool and rigidify.

Patient may bite into tray when soft to register a closed bite impression. Patient may also grind a full range of motion into a tray at this point.

Once rigid, the separation layer, together with the covering, are removed from the sheet of thermosetting material which then forms the custom dental impression tray. Impression material is then placed within the resulting dental impression tray and a final impression of the affected area in the patient's mouth is taken in the conventional fashion.

Conversely, for denture work, it is necessary to form a preliminary mold of the patient's mouth. The dental impression tray is then molded around this preliminary mold in order to form the dental impression tray. Thereafter, the wax covering and optionally a separation layer are removed, the tray filled with a dental impression material and a mold of the patient's gum area is taken in the conventional fashion.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 1 is a fragmentary crossectional view illustrating a preferred embodiment of the dental impression tray of the present invention;

FIG. 2 is a crossectional view, but showing the dental impression tray molded around the affected area of a patient's mouth;

FIG. 3 is a view similar to FIG. 2, but showing the dental impression tray removed from the patient's mouth after an impression has been taken; and FIG. 4 is a view similar to FIG. 2, but illustrating the dental impression tray of the present invention used to take a final impression of the affected area of the patient's mouth.

DETAILED DESCRIPTION OF A PREFERRED EMBODIMENT OF THE PRESENT INVENTION

With reference first to FIG. 1, a preferred embodiment of the dental impression tray assembly 10 is thereshown and comprises a flat sheet 12 of thermosetting material. This thermosetting material becomes pliable at a temperature of between 115°-150° F. but rigidifies at the temperature of the human mouth.

In the preferred form of the invention, polycapractone is used as the thermosetting sheet 12. Polycapractone becomes pliable in the temperature range of 136°-140° F. but rigidifies at the normal temperature of the mouth, i.e. about 98° F. Polycapractone is available from Interox America, 1230 Battleground Road, Deer Park, Tex. 77536, under the trademark CAPA 650.

Still referring to FIG. 1, a separation layer 14 overlies and covers one side 16 of the thermosetting sheet 12. This separation layer 14 can be constructed from any flexible material, such as one or more layers of gauze. The purpose of the separation layer 14 will be subsequently described.

A wax covering 18 is then disposed on the other side 20 of the separation layer 14. This covering 18 is also pliable when heated to 115°-150°. Consequently, when the tray assembly 10 is heated to 115°-150° F., the thermosetting sheet 12, separation layer 14 and wax covering 18 can be molded and manipulated by the dentist as desired.

The dental impression tray assembly of the present invention will first be described for use with bridge or crown prosthesis. With reference then to FIG. 2, the dental impression tray assembly 10 is first heated to a temperature of between 115°-150° F. and is then placed within the patient's mouth and around one or more of the patient's teeth 22. The tray 10 is molded into a generally U-shaped form so that the wax covering 18 faces and covers the affected area of the mouth while the thermosetting sheet 12, of course, is disposed around the wax covering 18. When molding the tray assembly 10 as shown in FIG. 2, the dentist carefully presses the pliable dental tray against the teeth 22 and adjacent mouth structure in order to form an appropriate mold.

Although the thermosetting sheet 12 remains pliable for an extended period of time, in some cases the sheet 12 may rigidify before the mold of the affected area of the mouth is completed. When this occurs, the dental tray 10 is simply removed from the patient's mouth, reheated to 115°-150° F., then reinserted into the mouth where the molding process is continued.

After the tray assembly 10 has been molded around the affected area of the mouth as shown in FIG. 2 and rigidified, it is removed from the mouth. At this time, however, gaps may exist between the covering 18 (FIG. 2) and the tooth 22 so that the covering 18 only approximates the shape of the tooth 22 and adjacent mouth structure. The separation sheet 14, together with the covering 18, is then removed from the thermosetting sheet 12 as indicated by arrow 24. After removal of the layer 14 and covering 18, the remaining thermosetting sheet 12, now molded, forms custom dental impression tray 30.

The thickness of the covering 18 is substantially uniform. Consequently, once the covering 18 and separation layer 14 are removed from the thermosetting sheet 12 as shown in FIG. 3, the remaining custom tray contains an impression of the affected area of the patient's mouth but is somewhat larger, due to the thickness of the covering 18, than the affected area of the patient's mouth.

With reference now to FIG. 4, dental impression material 26, such as silicone, is then placed within the interior 28 of the custom impression tray 30. The custom tray 30 is then placed within the affected area of the patient's mouth as shown in FIG. 4 so that the impression material 26 fills the space previously occupied by the covering 18 and separation layer 14 and forms a final impression. As is well known, the impression material 26 more accurately replicates the shape of the tooth 22 than the covering 18.

Once the impression material 26 hardens, the custom tray 30 together with the impression material 26 are removed from the patient's mouth and the final or working model of the affected area of the patient's mouth is constructed in the conventional fashion. Thereafter, the bridge work and/or crown is also constructed in a conventional fashion so that a further description thereof is unnecessary.

The dental impression tray assembly 10 of the present invention can also be used to form an impression for dentures. Since the gum area of the mouth is relatively soft, however, it is first necessary to form a preliminary mold of the patient's gum area and then to mold the dental impression tray assembly 10 as shown in FIGS. 2 and 3 around the preliminary mold rather than directly in the patient's mouth. Otherwise, the above procedure is identical so that a further description is not necessary.

The dental impression tray of the present invention is thus advantageous in several different respects. First, the dental impression tray of the present invention can be easily and rapidly molded in the patient's mouth. Furthermore, as previously described, even in the event that the thermosetting sheet 12 cools and becomes rigid during the molding process, it can be simply reheated and the molding process can be continued.

A still further advantage of Applicant's invention is that only a small amount of dental impression material 26 is necessary in order to make the final impression. Since such material is relatively expensive, substantial cost savings are achieved.

Having described my invention, however, many modifications thereto will become apparent to those skilled in the art to which it pertains without deviation from the spirit of the invention as defined by the scope of the appended claims.

I claim:

1. A custom impression dental tray assembly consisting of:

a sheet of thermosetting material becoming pliable at a temperature in the range of 115°-150° F. and rigid at the temperature of the mouth, said thermosetting material composed of polycapractone, a separation layer having one side directly contacting, overlying, covering and attached to one side of said sheet of thermosetting material, said separation layer composed of a sheet of gauze, a pliable wax covering on the other side of said separation layer, directly contacting said layer, said wax covering being moldable with said sheet of thermosetting material and having a substantially uniform thickness, said sheet, said separation layer and said wax covering forming an integral structure, wherein, after said tray assembly is heated and molded into the desired shape, said separation layer enables said separation layer and said wax covering to be removed from said sheet of thermosetting material which forms a custom impression tray.

* * * * *